United States Patent [19]

Kaminski et al.

[11] 4,045,578

[45] Aug. 30, 1977

[54] N-CHLORO-AMINO ACID DERIVATIVES EXHIBITING ANTIBACTERIAL ACTIVITY

[75] Inventors: James J. Kaminski; Nicolae S. Bodor, both of Lawrence, Kans.

[73] Assignee: INTERx Research Corporation, Lawrence, Kans.

[21] Appl. No.: 664,697

[22] Filed: Mar. 8, 1976

Related U.S. Application Data

[62] Division of Ser. No. 479,560, June 14, 1974, Pat. No. 3,966,796.

[51] Int. Cl.$^2$ .............................................. A01N 9/24
[52] U.S. Cl. .............................. 424/311; 260/482 R; 424/177
[58] Field of Search ............... 424/311, 300, 320, 177; 260/482 R

[56] References Cited

U.S. PATENT DOCUMENTS

| | | | |
|---|---|---|---|
| 3,530,162 | 9/1970 | Fuchs .............................. | 260/482 R |
| 3,966,796 | 6/1976 | Kaminski et al. ................ | 260/482 R |

Primary Examiner—V. D. Turner
Attorney, Agent, or Firm—Charles N. Blitzer

[57] ABSTRACT

There is provided, a novel class of compounds exhibiting antibacterial activity, said compounds having the formula:

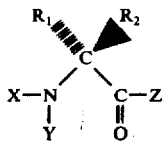

wherein X and Y each represent a member which may be the same or different selected from the group consisting of H and Cl with the proviso that X and Y cannot represent H simultaneously; $R_1$ and $R_2$ each represent a member which may be the same or different selected from the group consisting of an n- or branched alkyl group of from 1 to 20 carbon atoms, an aryl group (phenyl, naphthyl, etc.)

and a $(CH_2)_n$ group, wherein $n$ represents an integer of from 2 - 5; and Z represents a member selected from the group consisting of an —$OR_3$ group,

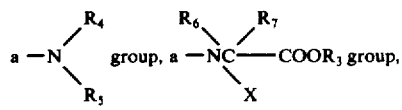

wherein $R_4$ and $R_5$ each represent a member which may be the same or different selected from the group consisting of H and an alkyl group of from 1 - 3 carbon atoms, wherein $R_6$ and $R_7$ each represent a member which may be the same or different selected from the group consisting of $R_1$, $R_2$, or H when X is not Cl or $R_1$ and $R_2$ when X is Cl, wherein $R_1$ and $R_2$ are as defined above, wherein X is as defined above, and wherein $R_3$ in each case represents a member selected from the group consisting of an n- or branched alkyl group of from 2 - 20 carbon atoms, a —$OCH_2CH_2$—$(OCH_2CH_2)_n$—$OR_1$ group, wherein $R_1$ is defined as above and $n$ represents an integer of from 1 - 11,

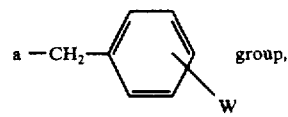

wherein W represents a member selected from the group consisting of H, an- or branched alkyl group of from 1 - 20 carbon atoms, a halogen atom (Cl, Br, I), an —$OR_8$ group,

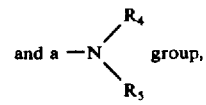

wherein $R_4$ and $R_5$ are as defined above and $R_8$ represents a member selected from the group consisting of H and $R_1$, wherein $R_1$ is as defined above,

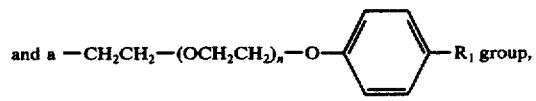

wherein $n$ represents an integer of from 1 - 20 and $R_1$ is as defined above,
with the further proviso that when X and Y are Cl and $R_1$ and $R_2$ are methyl, Z cannot be a member selected from the group consisting of —$OCH_3$ and $NH_2$.

12 Claims, No Drawings

N-CHLORO-AMINO ACID DERIVATIVES EXHIBITING ANTIBACTERIAL ACTIVITY

CROSS-REFERENCE TO RELATED APPLICATIONs

This application is a divisional application of our earlier co-pending application, Ser. No. 479,560, filed June 14, 1974, now U.S. Pat. No. 3,966,796.

BACKGROUND OF THE INVENTION

1. Field of the Invention

The present invention is directed to a novel class of antibacterial compounds and more specifically, the present invention is directed to a novel class of antibacterial compounds which are termed N-chloroamino acid derivatives as described later. The term "antibacterial" as employed in this application, includes both "antifungal" and "antibacterial" activity.

2. Description of the Prior Art

N-chlorinated naturally occurring amino acids as well as their derivatives are presently known. However, in the main, these compounds have not been isolated, or if isolated, can undergo rapid and often explosive decomposition. Illustrative of such a compound undergoing explosive decomposition upon isolation is methyl N-chlorosarcosinoate. Unpublished data, James J. Kaminski and Nicolae S. Bodor, Nov. 1, 1972.

Similarly, simple chloramines (e.g., chloramine per se) can undergo disproportionation, providing as one by-product $NCl_3$, a well-known toxic material.

Due to the low water solubility and low boiling point of simple chloramines, they simply evaporate too quickly from an aqueous solution, and as such, a sterilizing aqueous solution containing a simple chloramine is characterized by extremely low persistency.

Moreover, the simple chloramines (e.g., $NH_2Cl$, $NHCl_2$) are known to be readily deactivated by denaturing agents (e.g., horse serum), thus quickly diminishing the antibacterial activity of such compounds.

Methyl-α-N,N-dichloroaminoisobutyrate is also known, but only to the extent that it has been used to study the mechanism and kinetics of the dimerization of N,N-dichloro derivatives in strong bases. As such, no known utility has been recognized for this compound. See, A. M. Pinchuk, L. N. Markovskii and G. K. Bespalko, Zh. Org. Khim., 7, 2263 (1971).

SUMMARY OF THE INVENTION

Accordingly, it is one object of the present invention to provide a novel class of compounds exhibiting substantial antibacterial and antifungal activity.

It is another object of the present invention to provide a novel class of antibacterial compounds which will exhibit enhanced stability in the "neat" state.

Still, it is another object of the present invention to provide a novel class of antibacterial compounds which will exhibit enhanced stability in the "neat" state, in addition to further exhibiting substantial antibacterial activity over varying pH conditions.

Still further, it is another object of the present invention to provide a novel class of antibacterial compounds which remain stable in the "neat" state, remain active over varying pH conditions and yet fail to be inactivated as antibacterial agents by conventional denaturants, such as blood serum.

Finally, it is the last object of the present invention to provide a novel class of antibacterial compounds as heretofore described which are biodegraded into non-toxic products.

Accordingly, all the above objects of the present invention can be satisfied with a novel class of antibacterial compounds having the formula:

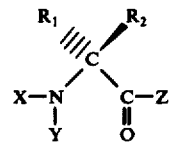

wherein X and Y each represent a member which may be the same or different selected from the group consisting of H and Cl with the proviso that X and Y cannot represent H simultaneously; $R_1$ and $R_2$ each represent a member which may be the same or different selected from the group consisting of an n- or branched alkyl group of from 1 to 20 carbon atoms, an aryl group (phenyl, naphthyl, etc.)

and a $(CH_2)_n$ group, wherein $n$ represents an integer of from 2 – 5; and Z represents a member selected from the group consisting of an $-OR_3$ group,

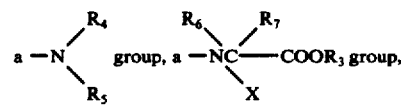

wherein $R_4$ and $R_5$ each represent a member which may be the same or different selected from the group consisting of H and an alkyl group of from 1 –3 carbon atoms, wherein $R_6$ and $R_7$ each represent a member which may be the same or different selected from the group consisting of $R_1$, $R_2$, or H when X is not Cl or $R_1$ and $R_2$ when X is Cl, wherein $R_1$ and $R_2$ are as defined above, wherein X is as defined above, and wherein $R_3$ in each case represents a member selected from the group consisting of an n- or branched alkyl group of from 2 – 20 carbon atoms, a $-OCH_2CH_2-(OCH_2CH_2)_n-OR_1$ group, wherein $R_1$ is defined as above and $n$ represents an integer of from 1 – 11,

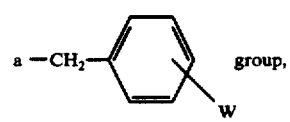

wherein W represents a member selected from the group consisting of H, an n- or branched alkyl group of from 1 – 20 carbon atoms, a halogen atom (Cl, Br, I), an $-OR_8$ group,

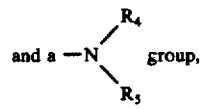

wherein $R_4$ and $R_5$ are as defined above and $R_8$ represents a member selected from the group consisting of H and $R_1$, wherein $R_1$ is as defined above,

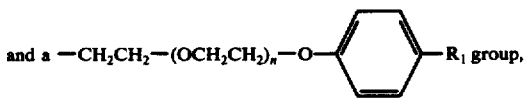

and a $-CH_2CH_2-(OCH_2CH_2)_n-O-\phi-R_1$ group, wherein $n$ represents an integer of from 1 – 20 and $R_1$ is as defined above, with the further proviso that when X and Y are Cl and $R_1$ and $R_2$ are methyl, Z cannot be a member selected from the group of $OCH_3$ and $NH_2$.

DETAILED DESCRIPTION OF THE INVENTION

In the above formula, when $R_1$, $R_2$, $R_6$, $R_7$ and $R_8$ represents an alkyl group, a carbon range of from 1 – 5 carbon atoms is preferred. When $R_1$ and $R_2$ represent an aryl group or a $(CH_2)_n$, respectively, phenyl is the aryl group of choice and 4 is the integer of choice for $n$.

At this point, it should be emphasized that the present invention not only covers the compounds included in the above generic formula, but in addition, covers a method for inhibiting bacterial growth with the above-identified compounds and the compound methyl-α-N,N-dichloroaminoisobutyrate (referred to earlier) as this compound has never been shown to exhibit antibacterial properties.

While all the compounds encompassed within the above-described generic formula will satisfy the objectives of the present invention, nevertheless, certain compounds are preferred as set out below:

(1) n-hexyl-α-N-chloroaminoisobutyrate
(2) n-octyl-α-N-chloroaminoisobutyrate
(3) n-dodecyl-α-N-chloroaminoisobutyrate
(4) n-tetradecyl-α-N-chloroaminoisobutyrate
(5) n-hexadecyl-α-N-chloroaminoisobutyrate
(6) n-octadecyl-α-N-chloroaminoisobutyrate
(7) Benzyl-α-N,N-dichloroaminoisobutyrate
(8) Ethyl-α-N,N-dichloroaminoisobutyrate
(9) Propyl-α-N,N-dichloroaminoisobutyrate
(10) n-butyl-α-N,N-dichloroaminoisobutyrate
(11) tert-butyl-α-N,N-dichloroaminoisobutyrate
(12) n-pentyl-α-N,N-dichloroaminoisobutyrate
(13) n-hexyl-α-N,N,-dichloroaminoisobutyrate
(14) n-octyl-α-N,N-dichloroaminoisobutyrate
(15) n-dodecyl-α-N,N-dichloroaminoisobutyrate
(16) n-tetradecyl-α-N,N-dichloroaminoisobutyrate
(17) n-hexadecyl-α-N,N-dichloroaminoisobutyrate
(18) n-octadecyl-α-N,N-dichloroaminoisobutyrate
(19) Esters of α-N,N-dichloroaminoisobutyric acid having the formula:

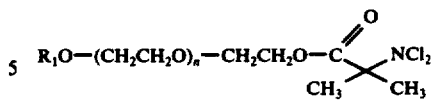

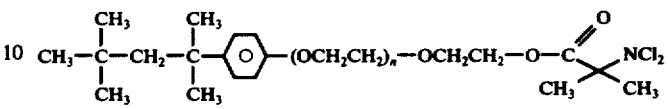

wherein $R_1$ is as previously defined and wherein $n$ represents an integer of from 1 – 11.

(20) Methyl-α-N,N-dichloroaminoisobutyrylglycinate
(21) Ethyl-α-N,N-dichloroaminoisobutyrylglycinate
(22) α-N,N-dichloroaminoisobutyryl-N'-methylamide.
(23) Esters of α-N-chloroaminoisobutyric acid having the formula:

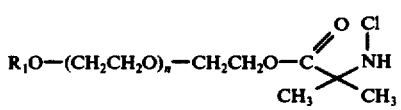

and

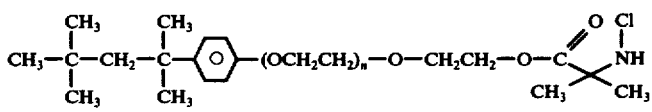

wherein $R_1$ is as previously defined, and wherein $n$ represents an integer of from 1 to 11.

The compounds of the present invention can be prepared by simple stepwise procedures as outlined below.

Firstly, the amino acid basic precursor compound is prepared in accordance with the equation set out below, wherein $R_1$ and $R_2$ are defined as above.

Any ordinary skilled artisan will clearly understand the preparatory scheme noted above for preparing the amino acid basic precursor compounds by the reaction of an appropriate ketone with ammonium chloride and potassium cyanide to give the corresponding amino acids, the derivatives of which are the object of the instant invention. See, J. P. Greenstein and M. Winitz, "Chemistry of the Amino Acids," Volume 1, J. Wiley and Sons, New York, New York, pp. 697–714 and references cited therein and A. Strecker, Ann., 75, 27 (1850), respectively.

The compounds of this invention fall into three general classes which are derived from the basic amino acid precursor compounds described above.

CLASS A (ESTERS)

The appropriate basic amino acid precursor compound is esterified, employing conventional methods for esterifying amino acids. For instance, the thionyl chloride method (see, Greenstein and Winitz, supra) or the acyl chloride method (see, Greenstein & Winitz, supra) are illustrative, but not limitative of those conventional methods which can be employed.

CLASS B (AMIDES)

The basic amino acid precursor compound is converted into the amine using conventional means. For instance, the corresponding amino acid chloride hydrochloride can be reacted with the appropriate amine, or aminolysis of the corresponding amino acid ester can occur. See, Greenstein and Winitz, supra.

CLASS C (DIPETIDES)

A suitable N-protected basic precursor amino acid compound is employed and coupled with the appropriate amino acid ester to give the corresponding N-protected dipeptide ester. Subsequently, conventional removal of the N-protective group results in the desired dipeptide. As N-protective groups, any conventional protective group is suitable. Illustrative of such protective groups are carbobenzoxy (CbZ), formyl, tert-butyloxycarbonyl (t-BOC) and the like. However, the formyl group is preferred.

Conventional coupling methods can be employed using conventional coupling agents, e.g., dicyclohexylcarbodiimide (DCCI), 1-ethoxycarboxyl-2-ethyl-dihydroquinoline (EEDQ), or coupling can be carried out using the "mixed" anhydride method. See, Greenstein and Winitz, supra. Cleavage of the N-protective group following coupling is then achieved using conventional methods suitable for the N-protective group, e.g., catalytic hydrogenation in the case of CbZ and t-BOC, or acid cleavage in the case of N-formyl.

Chlorination for all three classes of compounds (A, B, and C) can be carried out essentially under the same conditions described above using conventional chlorinating agents, e.g., chlorine, NaOCl, t-BuOCl, N-chlorosuccinimide, etc. The skilled artisan will readily appreciate the fact that the above-mentioned chlorinating agents are only illustrative and nonlimitative as other chlorinating agents can be employed as well.

Chlorination is normally carried out in a homogeneous solution or suspension at atmospheric pressure and at a temperature of from 0° C to 25° C, over a period of time, ranging from 0.5 to 5.0 hours.

Chlorination will normally be carried out in a water solvent, except in the case of t-BuOCl. In this situation, anhydrous organic solvents can be employed (e.g., benzene and/or t-Butyl alcohol).

Following chlorination, the chlorinated compound is isolated normally by filtration or extraction in a non-water miscible solvent such as ether, dichloromethane, petroleum ether, or the like. The final compound is purified by conventional methods such as vacuum distillation, sublimation, crystallization, or conventional chromatographic procedures.

Under the above chlorinating conditions, the N,N-dichloroamino compounds are normally obtained; however, the monochloro species can also be obtained in certain instances, and namely, when the pH of the reaction mixture is equal to or greater than 9.0.

Without further elaboration, it is believed that one skilled in the art can, using the preceding description, utilize the present invention to its fullest extent. The following preferred specific embodiments are, therefore, to be construed as simply illustrative, and not limitative of the remainder of the specification and claims in any way whatsoever. Reference to temperature, in all instances, refers to Centigrade unless otherwise indicated.

EXAMPLES

PREPARATION OF THE ESTERS (1) Preparation of n-hexyl-α-aminoisobutyrate hydrochloride: To 97.1 g (0.47 mol) phosphorus pentachloride suspended in 940 ml acetyl chloride there was added 48.4 g (0.47 mol) of α-aminoisobutyric acid and the resulting suspension was stirred at room temperature overnight. The amino acid chloride hydrochloride was removed from the reaction mixture by filtration and thoroughly washed with anhydrous ether under a nitrogen atmosphere. After drying in vacuo over calcium sulfate, the α-aminoisobutyryl chloride hydrochloride was obtained as a white powder, 72.96 g (0.46 mol), 98%, mp 139°–141° (dec), ir (KBr) 1750 (C=O) cm$^{-1}$.

Anal. Calcd for $C_4H_9Cl_2NO$: C, 30.40; H, 5.74; N, 8.89. Found: C, 31.24; H, 6.09; N, 9.15.

To 51.0 g (0.5 mol) n-hexyl alcohol heated to 40° was added in portions over 10 minutes with stirring 15.7 g (0.1 mol) of the above obtained α-aminoisobutyryl chloride hydrochloride. The reaction mixture was purged with nitrogen and maintained at 75° for 3 hrs. cooling to room temperature gave a liquid mass from which the excess n-hexyl alcohol was removed by distillation in vacuo, bp 34°–40° (0.4 mm). The amino acid ester hydrochloride crystallized by the addition of anhydrous ether and after trituration overnight was removed from the reaction mixture by filtration and thoroughly washed with anhydrous ether. After drying in vacuo over calcium sulfate, n-hexyl-α-aminoisobutyrate hydrochloride was obtained as a white solid, 12.2 g (0.055 mol), 55%, mp 74°–76°; ir (KBr) 1750 (C=O) cm$^{-1}$; pmr ($D_2O$) δ 1.07 (t, 3H), 1.3 (bs, 8H) and 4.23 (bt, 2H) ppm.

Anal. Calcd for $C_{10}H_{22}ClNO_2$: C, 53.68; H, 9.91; N, 6.26. Found: C, 53.27; H, 10.06; N, 6.10.

Following this procedure the ester derivatives described in Table I were prepared:

TABLE I $$\begin{array}{c} CH_3 \quad CH_3 \\ \diagdown \ \diagup \\ C \\ \diagup \quad \diagdown \\ H_3\overset{\oplus}{N} \quad CO_2(CH_2)_nCH_3 \\ Cl^{\ominus} \end{array}$$

| | | | | | Found: | | |
|---|---|---|---|---|---|---|---|
| n = | Anal. Calcd for: | C | H | N | C | H | N |
| 7 | $C_{12}H_{26}ClNO_2$ | 57.24 | 10.41 | 5.56 | 57.14 | 10.64 | 5.36 |
| 11 | $C_{16}H_{34}ClNO_2$ | 62.41 | 11.13 | 4.55 | 61.62 | 11.38 | 4.21 |
| 13 | $C_{18}H_{38}ClNO_2$ | 64.49 | 11.33 | 4.18 | 64.17 | 11.26 | 3.95 |
| 17 | $C_{22}H_{46}ClNO_2$ | 67.39 | 11.83 | 3.57 | 66.84 | 12.22 | 3.17 |

(2) Preparation of benzyl-α-aminoisobutyrate hydrochloride: To a suspension of 2.06 g (0.02 mol) of α-aminoisobutyric acid in 140 ml of benzyl alcohol at 5° C, there was added dropwise with stirring 15 ml of freshly distilled thionyl chloride over 0.5 hr. The reaction mixture was heated to and maintained at 125° C for 5 hr. The reaction solution was diluted to turbidity with anhydrous ether at room temperature and stored at 0° C overnight. The amino acid ester hydrochloride was removed from the reaction mixture by filtration and thoroughly washed with anhydrous ether. After drying in vacuo over calcium sulfate, benzyl-α-aminoisobutyrate hydrochloride was obtained as a white crystalline solid, 3.07 g (0.13 mol), 65%, mp 153°–155° C acetone:-hexane; ir (KBr) 1750 (C=O) cm$^{-1}$; pmr (D$_2$O) δ 1.60 (s, 6H), 5.23 (s, 2H) and 7.37 (s, 5H) ppm.

Anal. Calcd. for C$_{11}$H$_{16}$ClNO$_2$: C, 57.51; H, 7.02; N, 6.10. Found: C, 57.20; H, 7.12; N, 6.14.

(3) Preparation of methyl-α-aminoisobutyrate hydrochloride: To 30 ml (0.78 mol) of anhydrous methanol at −10° C was added to 7.9 ml (0.11 mol) of thionyl chloride at such a rate that the temperature was maintained below 0° C during the addition. 10.3 g (0.10 mol) of α-aminoisobutyric acid was added in portions with stirring also at a rate such that the temperature was maintained below −5° C during the addition. The reaction mixture was heated to and maintained at 58°–60° C for 2.5 hr. The methanol was removed under reduced pressure to afford a pale yellow viscous liquid which crystallized to an off-white solution standing at room temperature. Trituration of this solid with anhydrous ether gave methyl-α-aminoisobutyrate hydrochloride as a white crystalline solid, 15.3 g (0.099 mol), 99%, mp 185°–187° C, ir (KBr) 1735 (C=O) cm$^{-1}$; pmr (D$_2$O) δ 1.63 (s, 6H) and 3.87 (s, 3H) ppm.

Anal. Calcd. for C$_5$H$_{12}$ClNO$_2$: C, 39.09; H, 7.88; N, 9.12. Found: C, 39.24; H, 8.01; N, 9.26.

(4) Preparation of n-hexyl-α-N-chloroaminoisobutyrate: To 65 ml of 0.75 M sodium hypochlorite at 0° C there was added in portions over 5 minutes 4.46 g (0.02 mol) of n-hexyl-α-aminoisobutyrate hydrochloride. The suspension was vigorously stirred at 0° C for 1 hr. The N-chloramine was extracted into ether and the extracts combined and dried over anhydrous sodium sulfate. Following filtration, the ether was removed under reduced pressure to afford 4.12 g (0.019 mol), 95%, of n-hexyl-α-N-chloroaminoisobutyrate as a pale yellow liquid, ir (neat) 3280 (N—H and 1735 (C=O) cm$^{-1}$; pmr (CDCl$_3$) δ 5.0 (s, 1H), 4.2 (t, 2H), 1.43 (s, 6H), 1.32 (bs, 8H) and 0.93 (6t, 3H) ppm.

Anal. Calcd for C$_{10}$H$_{20}$ClNO$_2$: C, 54.16; H, 9.09; N, 6.32. Found: C, 54.29; H, 9.21; N, 5.92.

Following this procedure, thhe monochloroamino derivatives described in Table II were prepared:

with benzene:petroleum ether (30°–60° C), 75:25 gave n-hexyl-α-N,N-dichloroaminoisobutyrate as a dark yellow liquid, r$_f$=0.67 benzene, ir (neat) 1750 (C=O) cm$^{-1}$, pmr (CDCl$_3$) δ 4.2 (t, 2H), 1.63 (s, 6H), 1.30 (bs, 8H) and 0.90 (bt, 3H) ppm.

Anal. Calcd for C$_{10}$H$_{19}$Cl$_2$NO$_2$: C, 46.88; H, 7.48; N, 5.47. Found: C, 46.98; H, 7.69; N, 5.20.

Following this procedure, the dichloroamino derivatives described in Table II (supra) were prepared.

Following this procedure, the dichloroamino derivatives described in Table II (supra) were prepared.

(6) Preparation of benzyl-α-N,N-dichloroaminoisobutyrate: To 90 ml of 0.69 M sodium hypochlorite at 0° C, there was added dropwise with stirring 4.05 g (0.018 mol) of benzyl-α-aminoisobutyrate hydrochloride dissolved in 40 ml of water. The reaction mixture was adjusted to between a pH of 4 – 6 by the addition of 1 M HCl and the suspension was vigorously stirred at 0° C for 1 hr. The N-chloramine was extracted into dichloromethane and the extracts combined and dried over anydrous sodium sulfate. Following filtration, the dichloromethane was removed under reduced pressure to afford a dark yellow liquid. Distillation gave 2.93 g (0.007 mol), 61% benzyl-α-N,N-dichloroaminoisobutyrate, bp 119°–21° C (0.8 mm) ir (neat) 1730 (C=O) cm$^{-1}$; pmr (CDCl$_3$) δ 1.63 (s, 6H), 5.23 (s, 2H) and 7.38 (s, 5H).

Anal. Calcd. for C$_{11}$H$_{13}$Cl$_2$NO$_2$: C, 50.50; H, 5.00; N, 5.34. Found: C, 50.29; H, 5.08; N, 5.21.

(7) Preparation of methyl-α-N,N-dichloroaminoisobutyrate: To 750 ml of 0.76 M sodium hypochlorite at 0° C, there was added dropwise with stirring 39.1 g (0.26 mol) of methyl-α-aminoisobutyrate hydrochloride dissolved in 75 ml of water. The reaction mixture was adjusted between a pH of 4 – 6 by the addition of 1 M HCl and the suspension was stirred at 0° C for 0.75 hr. The N-chloramine was extracted into dichloromethane and the extracts were combined and dried over anhydrous sodium sulfate. Following filtration, the dichloromethane was removed under reduced pressure to afford a dark yellow liquid. Distillation gave 33.48 g (0.18 mol), 69%, methyl-α-N,N-

TABLE II

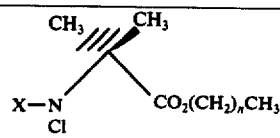

| x= | n= | Anal. Calcd for: | C | H | N | Found: | C | H | N |
|---|---|---|---|---|---|---|---|---|---|
| H | 7 | C$_{12}$H$_{24}$ClNO$_2$ | 57.70 | 9.68 | 5.61 | | 58.29 | 10.09 | 5.50 |
| Cl | 7 | C$_{12}$H$_{23}$Cl$_2$NO$_2$ | 50.71 | 8.16 | 4.93 | | 50.77 | 8.50 | 4.46 |
| H | 11 | C$_{16}$H$_{32}$ClNO$_2$ | 62.82 | 10.55 | 4.58 | | 63.79 | 11.24 | 4.62 |
| Cl | 11 | C$_{16}$H$_{31}$Cl$_2$NO$_2$ | 56.46 | 9.18 | 4.12 | | 56.74 | 9.51 | 3.81 |
| H | 13 | C$_{18}$H$_{36}$ClNO$_2$ | 64.74 | 10.87 | 4.20 | | 65.02 | 11.19 | 3.68 |
| Cl | 13 | C$_{18}$H$_{35}$Cl$_2$NO$_2$ | 58.68 | 9.58 | 3.80 | | 58.30 | 9.94 | 3.29 |
| H | 17 | C$_{22}$H$_{44}$ClNO$_2$ | 65.39 | 10.98 | 3.47 | | 67.77 | 11.67 | 2.99 |
| Cl | 17 | C$_{22}$H$_{43}$Cl$_2$NO$_2$ | 62.25 | 10.21 | 3.30 | | 61.69 | 10.53 | 2.80 |

(5) Preparation of n-hexyl-α-N,N-dichloroaminoisobutyrate: To 75 ml of 0.69 M sodium hypochlorite at 0° C there was added in portions over 5 minutes 4.46 g (0.02 mol) of n-hexyl-α-aminoisobutyrate hydrochloride. The reaction mixture was adjusted to a pH of 4–6 by the addition of 1 M HCl and the suspension was vigorously stirred at 0° C for 1 hr. The N-chloramine was extracted into dichloromethane and the extracts combined and dried over anhydrous sodium sulfate. Following filtration, the dichloromethane was removed under reduced pressure to afford 3.71 g (0.015 mol), 75% of a dark yellow liquid. Chromatography on a florisil column dichloroaminoisobutyrate, bp 34°–38° C (0.4 mm); ir (neat) 1750 (C=O) cm$^{-1}$, pmr (CDCl$_3$) δ 1.7 (s, 6H) and 3.87 (s, 3H).

Anal. Calcd. for C$_5$H$_9$Cl$_2$NO$_2$: C, 32.28; H, 4.88; N, 7.53. Found: C, 32.47; H, 5.03; N, 7.52.

(8) Preparation of methyl-1-N,N-dichloroamino-1-cyclopentanecarboxylate: To 30 ml of absolute methanol at 0° C, there was added dropwise with stirring over 0.5 hr. 7.9 ml of freshly distilled thionyl chloride. When the addition of thionyl chloride was completed, 12.9 g (0.1 mol) 1-amino-1-cyclopentanecarboxylic acid was added in portions over 0.25 hr. The suspension was heated with stirring, and the temperature maintained at 75° C for 2.5 hr. after solution of the reaction suspension. Removal of the methanol under reduced pressure gave an off-white crystalline mass. Trituration of this material with anhydrous ether gave 16.1 g (0.09 mol), 90%, methyl-1-amino-1-cyclopentanecarboxylate hydrochloride, mp 205°–207° C acetone:hexane, Kr (KBr) 1740 (C=O) cm$^{-1}$; pmr (D$_2$O) δ 3.95 (s, 3H) and 2.83 – 1.66 (m, 8H) ppm.

Anal. Calcd. for C$_7$H$_{14}$ClNO$_2$: C, 46.80; H, 7.85; N, 7.80. Found: C, 46.56; H, 7.55; N, 7.58.

To 65 ml of 0.76 M sodium hypochlorite at 0° C, there was added in portions over 5 minutes 3.58 g (0.02 mol) of the methyl-1-amino-1-cyclopentanecarboxylate hydrochloride obtained above. The reaction mixture was adjusted to a pH of 4 – 6 by the addition of 1 N HCl and the suspension was vigorously stirred at 0° C for 0.75 hr. The N-chloramine was extracted into dichloromethane and the extracts were combined and dried over anhydrous sodium sulfate. Following filtration, the dichloromethane was removed under reduced pressure to afford a dark yellow liquid. Distillation gave 4.07 g (0.019 mol), 95%, methyl-1-N,N-dichloroamino-1-cyclopentanecarboxylate, bp 79°–80° C (0.6 mm); ir (neat) 1750 (C=O) cm$^{-1}$; pmr (CDCl$_3$) δ 3.83 (s, 3H) and 3.00 – 1.33 (m, 9H) ppm.

Anal. Calcd. for C$_7$H$_{11}$Cl$_2$NO$_2$: C, 39.64; H, 5.23; N, 6.61. Found: C, 40.15; H, 5.26; N, 6.34.

(9) Preparation of 2-(2-n-butoxyethoxy)-ethyl-α-aminoisobutyrate hydrochloride: To 81.0 g (0.5 mol) 2-(2-n-butoxyethoxy)-ethanol heated to 40° C was added in portions over 10 minutes with stirring 15.7 g (0.1 mol) of α-amino-isobutyryl chloride hydrochloride. The reaction mixture was purged with nitrogen and maintained at 75° C for 3 hrs. Cooling to room temperature gave a liquid mass from which the excess 2-(2-n-butoxyethoxy)-ethanol was removed by distillation in vacuo, bp 70°–74° C (0.25 mm). The amino acid ester hydrochloride crystallized by the addition of petroleum ether (30°–60°) and after trituration in anhydrous ether overnight was isolated by filtration and thoroughly washed with anhydrous ether. After drying in vacuo over calcium sulfate, 2-(2-n-butoxyethoxy)-ethyl α-aminoisobutyrate hydrochloride was obtained as a white solid, 24.0 g (0.085 mol), 85%, mp 55°–60° C.

Anal. Calcd. for C$_{12}$H$_{26}$ClNO$_4$: C, 50.78; H, 9.24; N, 4.94. Found: C, 50.39; H, 9.53; N, 5.00.

(10) Preparation of 2-(2-n-butoxyethoxy)-ethyl-α-N,N-dichloroaminoisobutyrate: To 75 ml of 0.75 M sodium hypochlorite at 0° there was added in portions over 5 minutes 7.1 g (0.025 mol) 2-(2-n-butoxyethoxy)-ethyl-α-aminoisobutyrate hydrochloride. The reaction mixture was adjusted to pH 4 – 6 by the addition of 1 M HCl and the suspension was vigorously stirred at 0° for 1 hr. The N-chloramine was extracted into dichloromethane and the extracts combined and dried over anhydrous sodium sulfate. Following filtration, the dichloromethane was removed under reduced pressure to afford 5.0 g (0.016 mol), 64%, of a dark yellow liquid. Chromotography on a florisil column with benzene:petroleum ether (30°–60° C), 75:25 gave 2-(2-n-butoxyethyoxy)-ethyl-α-N,N-dichloroaminoisobutyrate as a dark yellow liquid.

Anal. Calcd. for C$_{12}$H$_{23}$Cl$_2$NO$_4$: C, 45.58; H, 7.33; N, 4.43. Found: C, 46.05; H, 7.60; N, 4.22.

PREPARATION OF THE AMIDES (1) Preparation of N',N'-diethyl-α-N,N-dichloroaminoisobutyramide: To 100 ml of 0.69 M sodium hypochlorite at 0° C, there was added in portions with stirring over 5 minutes 6.79 g (0.035 mol) of N',N'-diethyl-α-aminoisobutyramide hydrochloride. The reaction mixture was adjusted between a pH of 4 – 6 by the addition of 1 M HCl. After 0.75 hr. at 0° C, the N-chloroamine was extracted into dichloromethane. The extracts were combined and dried over anhydrous sodium sulfate. Following filtration, the dichloromethane was removed under reduced pressure to afford 6.78 g (0.030 mol), 86%, N',N'-diethyl-α-N,N-dichloroaminoisobutyramide, uv (H$_2$O) λ 305 nm.

PREPARATION OF THE PEPTIDES (1) Preparation of ethyl-α-aminoisobutrylglycinate hydrochloride: To a solution of 10.3 gms (0.10 mol) of α-aminoisobutyric acid in 210 ml of 98% formic acid at 0° C, there was added dropwise with stirring 70 ml of acetic anhydride. After stirring at room temperature for 2 hr., 85 ml of ice water was added and the solution evaporated under reduced pressure to give an off-white solid. Recrystallization from absolute ethanol gave 11.2 g (0.085 mol), 85%, N-formyl-α-aminoisobutyric acid, mp 129.5°–131° C; pmr (D$_2$O) δ 1.50 (s, 6H), 4.06 (s, 2H) and 8.16 (s, 1H) ppm.

Anal. Calcd. for C$_5$H$_9$NO$_3$: C, 45.79; H, 6.92; N, 10.68. Found: C, 45.92; H, 6.78; N, 10.42.

To a suspension containing 6.55 g (0.05 mol) of the N-formyl-α-aminoisobutyric acid obtained above 6.98 g (0.05 ml) of ethyl glycinate hydrochloride and 5.07 g (0.05 mol) of triethylamine in 200 ml dichloromethane was added to 10.9 g (0.05 mol) of N,N-dicyclohexylcarbodiimide. The reaction mixture was stirred at room temperature overnight and the dicyclohexylurea (11.2 g) was removed by filtration. The filtrate was washed with 5 ml portions of water, 5% HCl and 5% NaHCO$_3$ and dried over anhydrous sodium sulfate. Following filtration, the dichloromethane was removed under reduced pressure to afford an off-white solid. Recrystallization from acetone-hexane gave 5.3 g (0.02 mol), 40%, ethyl-N-formyl-α-aminoisobutyrylglycinate, mp 94°–98° C; pmr (d$^6$-DMSO) δ 8.16 (bs, 2H), 7.96 (s, 1H), 4.10 (q, 2H), 3.76 (d, 2H), 1.43 (s, 6H) and 1.26 (t, 3H) ppm.

(2) Preparation of ethyl-α-N,N-dichloroaminoisobutyrylglycinate: To a solution of 2.16 g (0.01 mol) of ethyl-N-formyl-α-aminoisobutyrylglycinate in 50 ml of dry hydrogen chloride in tetrahydrofuran (1 M), there was added 1 g of 10% palladium-on-charcoal. The mixture was shaken at room temperature under an atmosphere of hydrogen at 50 psi for several days. Following filtration, the solvent was removed under reduced pressure to afford 1.18 g (0.005 mol), 50%, ethyl-α-aminoisobutyrylglycinate hydrochloride, pmr (D$_2$O) δ 4.43 (s, 2H), 4.33 (q, 2H), 1.70 (s, 6H) and 1.23 (t, 3H) ppm.

Through an aqueous solution of 1.18 g (0.005 mol) of the ethyl-α-aminoisobutyrylglycinate hydrochloride obtained above, maintained at 0° C, chlorine gas was bubbled through for 0.5 hr. The N-chloroamine was extracted into dichloromethane and the extracts combined and dried over anhydrous sodium sulfate. Following filtration, the dichloromethane was removed under reduced pressure to afford 0.94 g (0.0035 mol), 70%, ethyl-α-N,N-dichloroaminoisobutyrylglycinate, uv ($H_2O$) λ 305 nm; pmr ($CDCl_3$) δ 6.90; (bs, 1H), 4.23 (q, 2H), 4.10 (d, 2H), 1.70 (s, 6H) and 1.30 (t, 3H) ppm.

The preceding examples can be repeated with similar success by substituting the generically or specifically described reactants and/or operating conditions of this invention for those employed in the foregoing examples.

EXAMPLE II

(STABILITY OF METHYL-α-N,N-DICHLOROAMINOISOBUTYRATE IN THE NEAT STATE AT 40° C)

In Table III set out below, there is provided the stability data for the above-identified compound over a period of 70 days. Though not specifically set forth, similar stability data will be observed for the remaining compounds of this invention.

TABLE III
STABILITY OF METHYL-α-N,N-DICHLOROAMINOISOBUTYRATE IN THE NEAT STATE AT 40° C

| time (days) | Wt. (mg.)[a] | $V_T$(ml)[b] | % Cl[c] |
|---|---|---|---|
| 0 | 36.35 | 74.70 | 36.4 |
| 1 | 28.72 | 58.20 | 35.9 |
|   | 25.63 | 51.80 | 35.8 |
| 2 | 24.39 | 48.95 | 35.5 |
|   | 25.80 | 51.85 | 35.6 |
| 3 | 26.68 | 54.00 | 35.8 |
| 4 | 30.44 | 61.00 | 35.5 |
|   | 31.49 | 63.45 | 35.7 |
| 7 | 29.46 | 58.33 | 35.0 |
|   | 35.99 | 71.70 | 35.3 |
| 14 | 32.14 | 63.65 | 35.1 |
|   | 31.77 | 63.00 | 35.1 |
| 21 | 30.85 | 64.90 | 37.2 |
|   | 31.74 | 66.20 | 36.9 |
| 28 | 33.61 | 67.85 | 35.7 |
|   | 33.99 | 69.45 | 36.2 |
| 35 | 34.86 | 72.50 | 36.8 |
|   | 33.45 | 69.75 | 36.9 |
| 70 | 37.49 | 77.15 | 36.4 |

[a]Weight of sample analyzed in mg.
[b]Volume of $10^{-2}$ N sodium thiosulfate titrant used to analyze sample.
[c]Percent "positive" chlorine in sample analyzed.

EXAMPLE III

(ANTIBACTERIAL ACTIVITY OF METHYL-α-N,N-DICHLOROAMINOISOBUTYRATE)

In Table IV which follows, there is provided a review of the antibacterial activity of the above-identified compound over a wide pH range. As can be readily seen, in the presence of or in the absence of serum, the above-identified compound exhibits substantial antibacterial activity over a vast range of microbial organisms.

TABLE IV
ANTIBACTERIAL ACTIVITY, TIME (min.)

| COMPOUND AND CONDITIONS: | Staph. epidermidis | E. coli | Klebsiella pneumoniae | Pseudomonas aeruginosa | Staph. aureus | Salmonella typhimurium | Bordetella bronchiseptica | Bacillus subtilis |
|---|---|---|---|---|---|---|---|---|
| $Cl_2N-C(CH_3)_2-COOCH_3$ | | | | | | | | |
| in 0.1 M NaOAc, pH 4.6 without serum $0.77 \times 10^{-3}$M, 887 ppm, 334 ppm Cl+ | 1 | 0.5 | 0.5 | 0.5 | 1 | — | 0.5 | — |
| in 0.1 M NaOAc, pH 4.6 with serum $0.77 \times 10^{-3}$M, 887 ppm, 334 ppm Cl+ | 2 | 0.5 | 0.5 | 1 | 2 | — | 0.5 | — |
| in 0.1 M NaOAc, pH 4.6 without serum $0.76 \times 10^{-3}$M, 1071 ppm, 403 ppm Cl+ | 1 | 0.5 | 0.5 | 1 | 2 | — | 0.5 | — |
| in 0.1 M NaOAc, pH 4.6 with serum $0.00 \times 10^{-3}$M, 1116 ppm, 420 ppm Cl+ | 3 | 0.5 | 1 | 0.5 | 3 | — | 1 | — |
| in 0.1 M $NaH_2PO_4$, pH 7.0 without serum $0.75 \times 10^{-3}$, 1070 ppm, 403 ppm Cl+ | 3 | 1 | 1 | 3 | 4 | — | 1 | — |
| in 0.1 M $NaH_2PO_4$, pH 7.0 with serum $0.75 \times 10^{-3}$M, 1070 ppm, 403 ppm Cl+ | 4 | 0.5 | 1 | 0.5 | 4 | — | 0.5 | — |
| in 0.1 M $Na_2B_4O_7$, pH 8.8 $0.72 \times 10^{-3}$M, 1064 ppm, 400 ppm Cl+ without serum | | | | | | | | |
| in 0.1 M $Na_2B_4O_7$, pH 8.8 with serum $0.72 \times 10^{-3}$M, 1064 ppm, 400 ppm Cl+ | 4 | 1 | 3 | 2 | 7 | — | 3 | — |

THE ANTIBACTERIAL SCREEN

Test Solution

Immediately preceding the screen, the compound is weighed and diluted with a buffer or other solvent to give the final concentration desired. The buffer or solvent chosen depends on the conditions of the screen and could be one of the following: 0.1 M NaOAc, pH 4.6; 0.1 M $NaH_2PO_4$, pH 7.0; 0.1 M $Na_2B_4O_7$, pH 8.8; 35% methanol in one of the aforementioned buffers; 10% Triton X 100 in buffer, etc.

The positive chlorine concentration of the test solution is then determined iodometrically.

Cultures and Media

Media used for the Screen are Nutrient Broth, BBL No. 11479 and Nutrient Agar, BBL No. 11472 prepared according to label directions. The broth is dispensed in 75 ml amounts to flasks for overnight cultures and in 5 ml amounts to culture tubes for subculturing during the Screen. Agar plates are prepared as usual.

Overnight cultures are prepared by inoculating from stock cultures into the 75 ml flasks of nutrient broth and inoculating for 15 hrs. at 37° C.

The organisms ordinarily screened are:

*Staphylococcus aureus*  ATCC# 6538

| | |
|---|---|
| Staphylococcus epidermidis | ATCC# 12228 |
| Bacillus subtilis | ATCC# 6051-1 |
| Pseudomonas aeruginosa | ATCC# 9027 |
| Salmonella typhimurium | ATCC# 14028 |
| Klebsiella pneumoniae | ATCC# 10031 |
| Escherichia coli | ATCC# 10536 |
| Bordetella bronchiseptica | ATCC# 4617 |

The organisms are maintained as stock cultures on nutrient agar at 4° C. They are transferred and checked for purity monthly.

Procedure

The iodometrically characterized test solution is dispensed in 5 ml amounts to seven small stoppered flasks. The organisms are screened one at a time as follows:

A 0.2 ml portion of the overnight culture is inoculated into 5 ml of 0.9% NaCl for use in controls. A 0.2 ml portion of the overnight culture is inoculated into a flask containing 5 ml of the test solution, an automatic timer is simultaneously triggered and the solution mixed. In time intervals of 30 seconds, 1, 2, 3, 4, 5, 6, 7, 8, 9, and 10 minutes a loopful of the inoculated solution is subcultured into 5 ml of sterile nutrient broth and mixed by a Vortex Genie Mixer, the high dilution serving to stop the action of the compound. At the end of the ten minute screen, the entire procedure is repeated for each of the remaining six organisms. All of the subculture tubes are incubated at 37° C and checked for signs of growth by turbidity at 24 hr., 48 hr., 3, 5, and 7 days. The earliest subculture time at which no growth is present in the subculture tube is considered the endpoint and is recorded as that time, e.g., 7 minutes.

Controls

Viability of Stock Cultures — 0.2 ml of the stock culture is transferred to 5 ml of saline (to simulate 0.2 ml in 5 ml test solution), a loopful of this mixture is subcultured to 5 ml of nutrient broth as in the Screen and incubated at 37° C for 24 hr. Turbidity indicates that the organism would grow when not in the presence of the test solution.

Purity of Stock Cultures — a loopful of the stock culture in saline is streaked onto nutrient agar to insure the purity and identity of each culture (the cultures are also checked biochemically each month for this purpose).

Dilution of the Test Solution — a loopful of the test solution is diluted in a 5 ml amount of nutrient broth. A loopful of the organism in saline is inoculated into this tube. Turbidity after 24 hr. at 37° C indicates that the dilution of the test solution in the nutrient broth subculture during the Screen is great enough to stop the action of the compound.

Purity of Organisms in Test Solution — At the end of the Screen a loopful of the organism-test solution mixture is streaked onto nutrient agar to insure that contamination has not occurred during the 10 minutes period of the Screen. Often there is no growth at this time if the compound has effectively inhibited all the organisms.

Lack of Bacteriacidal Activity of Buffers and Other Solvents — Before a buffer or other solvent is used as the diluent it is screened against the organisms *Staphylococcus aureus*, ATCC No. 6538 and *Escherichia coli* ATCC No. 10536 (the 'strongest' and 'weakest' of the organisms) to insure that the buffer or solvent has no antibacterial activity in itself. Subculture times of 10, 20 and 30 minutes are used. Incubation conditions are the same.

Variations

Serum as a Denaturant of the Compound — the test solution is prepared and characterized as above but is made up at twice the concentration desired. The solution is diluted 1:1 with Rehydrated Tissue Culture Dessicated Horse Serum, Difco No. 5357-72 and disposed in a 5 ml amount to a small flask. The mixture is incubated at Room Temperature for 30 minutes to allow denaturation of the compound by the serum and then screened as above.

The 5 ml mixture of serum and test solution are prepared in sequence to allow as close to 30 minutes as possible before the beginning of the screen of each organism.

Variation of Conditions — each new compound is generally screened several times at different concentrations, different pH's, in different solvents and at each of those conditions with and without serum as a denaturant.

EXAMPLE IV (ANTIBACTERIAL ACTIVITY OF MYRISTYL-α-N-CHLOROAMINOISOBUTYRATE AND MYRISTYL-α-N,N-DICHLOROAMINOISOBUTYRATE, RESPECTIVELY)

In Table V which follows, there is provided data as to the antibacterial activity of the above-identified compounds at a pH of 7.0. The Table shows each respective compound to be substantially active against a wide range of micro-organisms.

TABLE V

| | Minimal Inhibitory Concentration pm | |
|---|---|---|
| Organism | *11,845 | Δ11,847 |
| S. aureus Smith | 1.6 | 62.5 |
| S. pyogenes C203 | 6.3 | 31.3 |
| E. coli Vogel | >250 | 500 |
| K. pneumoniae 39645 | >250 | 500 |
| P. mirabilis MGH-1 | >250 | 500 |
| Ps. aeruginosa MGH-2 | 250 | 125 |
| E. coli AB 1932-1 | >250 | 500 |
| E. coli 1100/B22 | >250 | 500 |
| A. niger 16404 | 250 | >62.5 |
| C. albicans 10231 | 250 | 125 |
| C. albicans Wisconsin | 250 | 125 |
| T. mentagrophytes 9129 | 125 | 7.8 |

*11,845 is n-tetradecyl-α-N-chloroaminoisobutyrate
Δ11,847 is n-tetradecyl-α-N,N-dichloroaminoisobutyrate THE ANTIBACTERIAL SCREEN (Autotiter IV)

Program I. In vitro antimicrobial screen.

1. Methodologies a) Compounds. All compounds to be screened are weighed (approx. 10 mg) on the day preceding the test date. Each compound is solubilized on the day of assay in appropriate solvent and diluted automatically in the Autotiter IV with distilled water (buffer can be employed here, also).

b) Organisms.

Bacteria: Staphylococcus aureus Smith (or 209), *Escherichia coli* AB 1932-1, 1100/B222 and Vogel, *Klebsiella pneumoniae* 39645, *Proteus mirabilis* MGH-1, *Pseudomonas aeruginosa* MGH-2 and *Streptococcus pyogenes* C203.

Fungi/Yeast: *Aspergillus niger* 14604, *Candida albicans* 10231 and Wisconsin and *Trichophyton mentagrophtes* 9129.

c) Inocula: Prior to utilization in the Autotiter IV, all bacteria are cultured for 18–20 hr. (37° C) in tryptose phosphate broth (TP), except, *S. pyrogenes* C203, which is cultured in Brain Heart Infusion broth plus 10% normal horse serum. Immediately prior to testing, each culture is adjusted to an optical density of 0.10 (650 nm), employing a Bausch & Lomb Spectronic 20, and diluted subsequently into double strength medium to approximately $2 \times 10^5$ viable organisms per ml.

Spore suspensions of the fungi, *A. niger* and *T. Mentagrophtes* are diluted into Maltose Peptone Broth ($2 \times$) to approx. $2 \times 10^5$ spores per mol. The *C. albicans* is adjusted to an optical density of 0.10 and diluted into double strength Maltose Peptone to approx. $2 \times 10^5$ organisms per ml.

d) Program for Routine Testing.

1. An automated injector system dispenses 0.05 ml of diluent (sterile H₂O or buffer) to all cups of the autotiter trays from rows 2 through 7.

2. The loops (for sequential dilutions of the compounds are moistened by immersion into 70% ethyl alcohol. After removal of excess alcohol by blotting, the loops are moved to the first row of cups in the autotray containing 0.10 ml of the compound to be diluted and tested (usually, this initial concentration is 500 to 1000 mcg/ml, but can be varied upward or downward). The loops are lowered and sequentially transfer the diluted solutions of the compound through row 7.

Immediately after each dilution made, each cup is automatically inoculated with 0.05 ml of the appropriate test organism. This inoculation derives from a second injector system containing the organism in doublestrength medium. The total operation consists of the automatic dilution of a single compound in each of 8 rows of the Autotiter try.

After these operations, we reverse the tray and a second compound is diluted over the other one-half of the tray and inoculated, subsequently, with 8 organisms. Thus, for each Autotiter Tray, two compounds are screened against 8 different organisms at dilutions ranging from 1:2 to 1:128.

e) Incubation. The inoculated Autotiter trays are incubated at 37° C for 18 – 20 hr. At the end of this period, each tray is examined for the presence or absence of growth (turbidity). The lowest concentration of the compound inhibiting growth is recorded as the minimal inhibitory concentration (MIC).

Yeast and fungi are tested in the same manner except that (i) Maltose Peptone broth is employed and, (ii) the Autotiter trays are sealed with plastic tape during the incubation period (250° C/5 days) to prevent evaporation.

From the foregoing description, one skilled in the art can easily ascertain the essential characteristics of this invention, and without departing from the spirit and scope thereof, can make various changes and modifications of the invention to adapt it to various usages and conditions. As such, such changes and modifications are properly, equitably, and intended to be, within the full range of equivalence of the following claims.

What we claim is:

1. A method for inhibiting bacterial growth which comprises applying thereto, an antibacterial effective amount of an ester of α-N,N-dichloroaminoisobutyric acid having the formula:

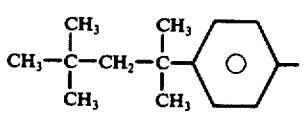

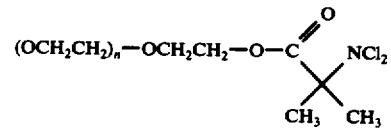

and

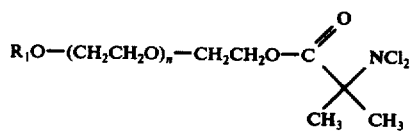

wherein $R_1$ represents a member selected from the group consisting of an n- or branched alkyl group of from 1 to 20 carbon atoms, a phenyl group and a naphthyl group; and wherein n represents an integer of from 1 to 11.

2. The method of claim 1, wherein $R_1$ represents an alkyl group of from 1 to 5 carbon atoms.

3. A method for inhibiting bacterial growth which comprises applying thereto, an antibacterial effective amount of a compound having the formula:

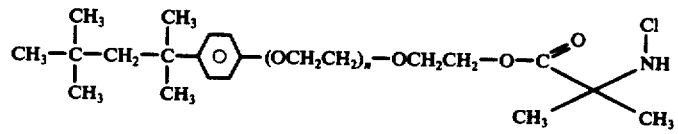

and

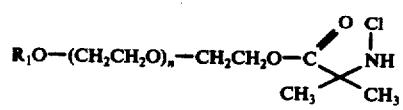

wherein $R_1$ represents a member selected from the group consisting of an n- or branched alkyl group of from 1 to 20 carbon atoms, a phenyl group and a naphthyl group; and wherein n represents an integer of from 1 to 11.

4. The method of claim 3, wherein $R_1$ represents an alkyl group of from 1 to 5 carbon atoms.

5. A method for inhibiting bacterial growth which comprises administering thereto, an antibacterial effective amount of the compound:

n-Hexyl-α-N-chloroaminoisobutyrate.

6. A method for inhibiting bacterial growth which comprises administering thereto, an antibacterial effective amount of the compound:

n-Octyl-α-N-chloroaminoisobutyrate.

7. A method for inhibiting bacterial growth which comprises administering thereto, an antibacterial effective amount of the compound:

n-Dodecyl-α-N-chloroaminoisobutyrate.

8. A method for inhibiting bacterial growth which comprises administering thereto, an antibacterial effective amount of the compound:

n-Tetradecyl-α-N-chloroaminoisobutyrate.

9. A method for inhibiting bacterial growth which comprises administering thereto an antibacterial effective amount of the compound:

n-Hexadecyl-α-N-chloroaminoisobutyrate.

10. A method for inhibiting bacterial growth which comprises administering thereto an antibacterial effective amount of the compound:

n-Octadecyl-α-N-chloroaminoisobutyrate.

11. A method for inhibiting bacterial growth which comprises administering thereto an antibacterial effective amount of the compound:

Methyl-α-N,N-dichloroaminoisobutyrylglycinate.

12. A method for inhibiting bacterial growth which comprises administering thereto an antibacterial effective amount of the compound:

Ethyl-α-N,N-dichloroaminoisobutyrylglycinate.

* * * * *